April 2, 1940. R. ENGLE Plant Pat. 372
CARNATION
Filed May 5, 1939
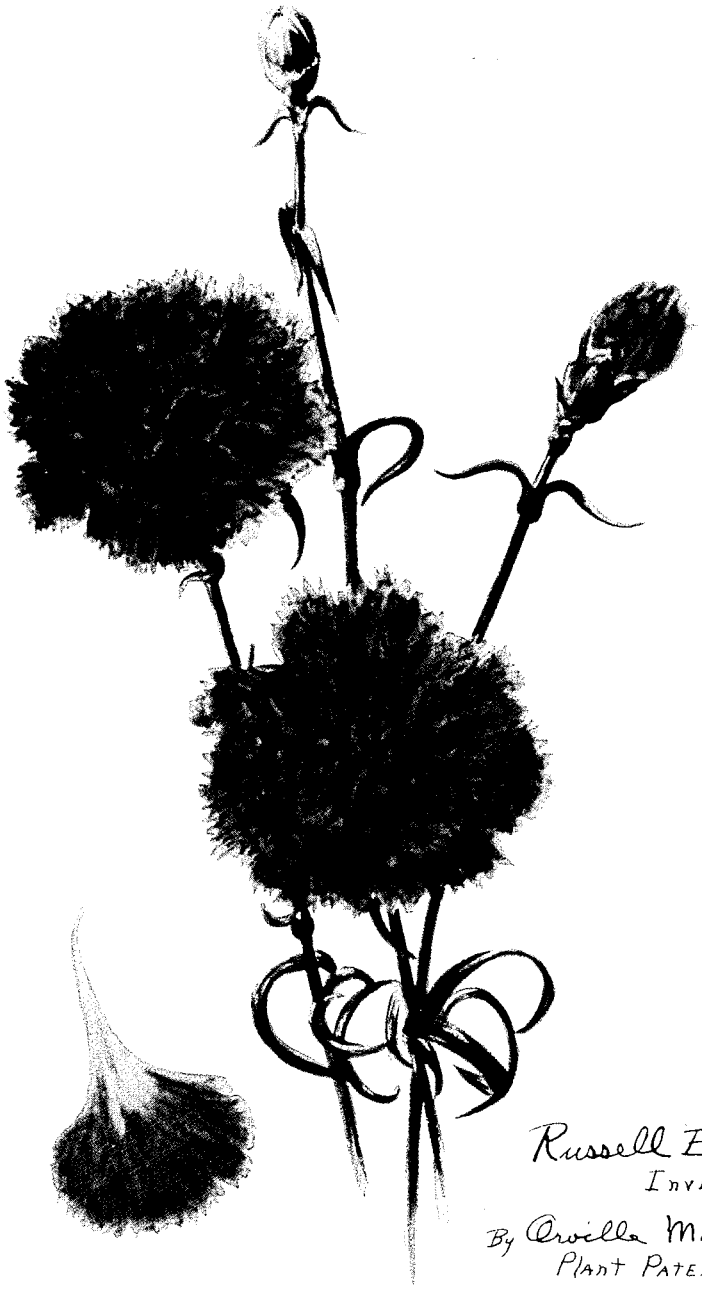
Russell Engle
INVENTOR
By Orville M. Kile
PLANT PATENT AGENT Patented Apr. 2, 1940

Plant Pat. 372

UNITED STATES PATENT OFFICE

372

CARNATION

Russell Engle, Kokomo, Ind., assignor to Tom Knipe, Kokomo, Ind.

Application May 5, 1939, Serial No. 272,001

1 Claim. (Cl. 47—60)

My present invention relates to improvements in perpetual blooming carnations of the color class commonly known as crimson and has special reference to improvements over the well-known variety Woburn.

My new variety is a result of definite breeding efforts and is a cross between Patrician and Woburn, the former being the female parent and the latter the male parent. It has been asexually reproduced for several years and has retained its distinctive characteristics.

The original illustrations accompanying the specification show in somewhat reduced size, two blossoms and two buds in various stages of opening, together with a portion of the stems and leaves. These are portrayed in approximately their natural colors although it must be understood that it is impossible for the artist to show the brilliance of this variety, particularly as seen in artificial light. Also shown is a single petal.

Color references are to Ridgway's Color Standards and Nomenclature, except where lack of plate reference makes it obvious that the ordinary dictionary term is intended.

Following is a more detailed description of this new variety.

*The plant*

Growth: Upright and very vigorous, attaining a height of about four feet. Free flowering and disease resistant. Cuttings root very freely.

Foliage: Plentiful but not grassy. Each leaf of the third pair from the blossom averages 2½ to 3 inches in length and ¼ inch wide.

Color.—Dark Dull Yellow Green (Plate XXXII), covered with gray bloom.

Stems: Long, straight and strong though slender. Amply strong to hold the large flowers in an upright position. About 4 feet long. Internodes exceptionally long.

Color.—Dusky Yellowish Green (Plate XLI), covered with gray bloom.

*The flower*

Bud: Slender and of uniform thickness. End blunt.

Blossom:

*Size.*—Large, averaging 3½ to 3¾ inches in diameter. The large size is due to the large size of the individual petals rather than to the number of petals.

*Form.*—Irregular; high-centered.

*Petalage.*—Number of petals in March is approximately 32.

*Petals.*—Irregularly serrated, sometimes deeply cut. Moderately crinkled, outer petals almost flat. Size—entire length of outer petals averages 2½ inches, being slightly more than 1½ inches from top to claw or shank. Width at widest portion of petal is 1½ to 1¾ inches. Color—central portion of petals is approximately Carmine (Plate I). Edges are slightly darker, lower portion slightly lighter. In artificial light the blossom assumes a brilliance, instead of appearing darker as is usual with other crimson carnation varieties. Aspect—the petals are of good substance and slightly velvety on their upper surfaces.

*Calyx.*—Exceedingly strong, no split ever having been observed. Consists of a single tube with five lobes. Spinach Green (Plate V) at top, Lettuce Green (Plate V) where covered by bracts.

*Bracts.*—Strong and large. Same color as upper part of calyx.

*Fragrance.*—Mild cinnamon fragrance.

*Longevity.*—Blossoms last exceedingly well as cut flowers.

*Reproductive organs*

Ovary: Very large; tough; ⅜ to ½ inch high; encloses many ovules.

Pistils: Two; pink tinted; curled at ends; 1½ inches long and sitting atop the ovary; usually have stipule-like appendages about two-thirds of the distance to the top. Length of entire pistil and ovary about two inches.

Stamens: Few; white; straggling and of varying lengths, but much shorter than pistils; anthers mostly lacking; some filaments topped with petal-like formations or petaloids.

*Comparison*

The variety which most resembles my new variety is its paternal parent, Woburn, and is similar to it in general appearance and color. However these two varieties differ in several important respects.

My new variety takes on a brilliance of color in artificial light instead of appearing darker as do Woburn and other crimson and carmine carnation varieties. My new variety is larger and slightly more irregular in outline than Woburn, Woburn being 3¼ to 3½ inches in diameter as compared with a diameter of 3½ to 4 inches for my new variety. My new variety branches and blooms much more freely than Woburn and produces a larger plant. I get three times the amount of bloom from my new variety as I do from Woburn, and at least fifty percent stronger plants, although the same comparison may not be true in all sections of the country. The cuttings of my new variety root readily in the propagation bench—a feature in which Woburn is very deficient. My new variety comes into crop much more quickly and blooms more freely after being transferred from the field to permanent blooming quarters in the greenhouses. The flowers of my new variety have pistils that are about twice as long as those of Woburn, not so dark a pink, and curled at the ends whereas those of Woburn are usually straight.

Having thus disclosed my invention, I claim:

A new and distict variety of carnation substantially as shown and described, characterized particularly by its vigorous growth; its quick and profuse blooming after being transferred from the field; the rapidity with which its cuttings are rooted; its strong, non-splitting calyx; and its very large, irregular flowers approximating carmine which appear much more brilliant in artificial light.

RUSSELL ENGLE.